United States Patent
Schiel

(10) Patent No.: US 10,558,612 B1
(45) Date of Patent: Feb. 11, 2020

(54) RELATIONAL DATABASE CONVERSION AND PURGE

(71) Applicant: CERNER INNOVATION, INC., Kansas City, KS (US)

(72) Inventor: Toby Schiel, Kansas City, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 223 days.

(21) Appl. No.: 15/831,020

(22) Filed: Dec. 4, 2017

(51) Int. Cl.
*G06F 16/11* (2019.01)
*H04L 29/08* (2006.01)
*G06F 16/172* (2019.01)
*G06F 16/28* (2019.01)
*G16H 10/00* (2018.01)

(52) U.S. Cl.
CPC .......... *G06F 16/119* (2019.01); *G06F 16/172* (2019.01); *G06F 16/284* (2019.01); *H04L 67/06* (2013.01); *G16H 10/00* (2018.01)

(58) Field of Classification Search
CPC .... G06F 16/119; G06F 16/172; G06F 16/284; H04L 67/06; G16H 10/00
See application file for complete search history.

(56) References Cited

U.S. PATENT DOCUMENTS

| | | | |
|---|---|---|---|
| 6,052,685 A * | 4/2000 | Eastwick | G06F 16/252 |
| 7,020,660 B2 | 3/2006 | Woodring | |
| 7,035,859 B2 * | 4/2006 | Fitzpatrick | G06F 16/2365 |
| 7,054,851 B2 | 5/2006 | Haley | |
| 7,136,883 B2 | 11/2006 | Flamma et al. | |
| 7,941,395 B2 | 5/2011 | Cassidy | |
| 2007/0121585 A1 * | 5/2007 | Morrissey | H04L 67/02 370/352 |
| 2009/0313682 A1 * | 12/2009 | Rajput | H04L 63/102 726/4 |
| 2010/0049556 A1 * | 2/2010 | Liu | G06Q 10/02 705/5 |
| 2010/0132017 A1 * | 5/2010 | Robinson | H04L 63/08 726/5 |
| 2015/0264019 A1 * | 9/2015 | Carroll | H04L 63/0428 726/26 |
| 2015/0293946 A1 * | 10/2015 | Fong | G06F 16/212 707/811 |
| 2016/0358264 A1 * | 12/2016 | Brightman | G06Q 40/06 |
| 2017/0063566 A1 * | 3/2017 | Seminario | H04L 12/2816 |
| 2018/0260458 A1 * | 9/2018 | Huang | G06F 16/258 |

OTHER PUBLICATIONS

Admin, Why FTP is Insecure?, pp. 1-3, Apr. 19 (Year: 2017).*

* cited by examiner

*Primary Examiner* — Albert M Phillips, III

(74) *Attorney, Agent, or Firm* — Shook Hardy & Bacon LLP

(57) ABSTRACT

A computer implemented method, system and media are provided to convert relational database files hosted on a client server to operating database files. The operating database files are transferred using FTP protocol to a remote archival server. A relational database is created from the transferred operating database files on the remote archival server.

20 Claims, 6 Drawing Sheets

RELATIONAL DATABASE CONVERSION AND PURGE

BACKGROUND

Relational databases contain large amounts of data and are costly and difficult to back-up and purge. Relational databases are used in the medical and pharmacy fields to store orders and personal information that will need to be accessed and queried at later for reporting and treatment of the person. Oftentimes, additional physical disc space must be added to a client server to maintain backup or historical files from the relational database. Adding physical disc space is costly and time consuming to maintain. Alternatively, client servers can transfer the files via a network to a backup or remote server in a cloud-computing environment via a network.

The historical files are transferred are transferred one line by one line in relational database format line by line via a network to the remote server. Transferring historical relational database files via a network to a remote hosted server such as one located in a cloud computing network is a very time consuming process, often needing to be done overnight. Furthermore, if the network is prone to interruptions, the process to transfer files to a remote hosted server has to start over from the beginning if it is interrupted causing an additional delay.

SUMMARY

Embodiments of the present invention provide methods and system for performing a historical purge on a relational database on a client server and quickly and efficiently exporting the relational database information via a network to remote servers including archival database server hosted in a cloud-computing environment.

The claimed invention relates to a system and method supporting computerized medical and pharmaceutical relational database systems. More specifically, the claimed invention relates to a system, method and computer readable media for to converting relational database files hosted on a client server to operating database files. The operating database files are transferred using FTP protocol to a remote archival server. A relational database is created from the transferred operating database files on the remote archival server.

The claimed solution is necessarily rooted in computerized electronic medical and pharmacy relational database technology in order to overcome a problem specifically arising in the realm of computer medical and pharmacy relational database technology. The claims address the problem of quickly and efficiently creating historical or backup files for medical and pharmaceutical relational database technology.

The claimed system and method of the present application represents a new paradigm in performing a historical purge of relational database containing thousands, if not millions of files. Not only does the claimed invention purge and transfer thousands of relational database in a timely and efficient manner, it does so such that same reporting techniques used on both active relational database files and archived files. This allows for reporting documentation to be the same on active relational database files and archived relational database files. Previously, it was a time consuming and error prone method of transferring the relational database records line by line to an archival or cloud-based environment.

The method and system for automatically purging relational database files into an archival database such as a cloud-based environment reduces the overall time to transfer relational database records. The relational database structure according to the new technology is more cost effective to maintain, as new physical servers do not need to be added to the active relational database environment physically located at a pharmacy, medical center or financial institution.

BRIEF DESCRIPTION OF THE DRAWINGS

Embodiments are described in detail below with reference to the attached drawing figures, wherein.

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for a system and method for creating a nested relationship between a high level object and a child object in a documentation template hierarchy for generating a dynamic medical narrative.

Figure 1:
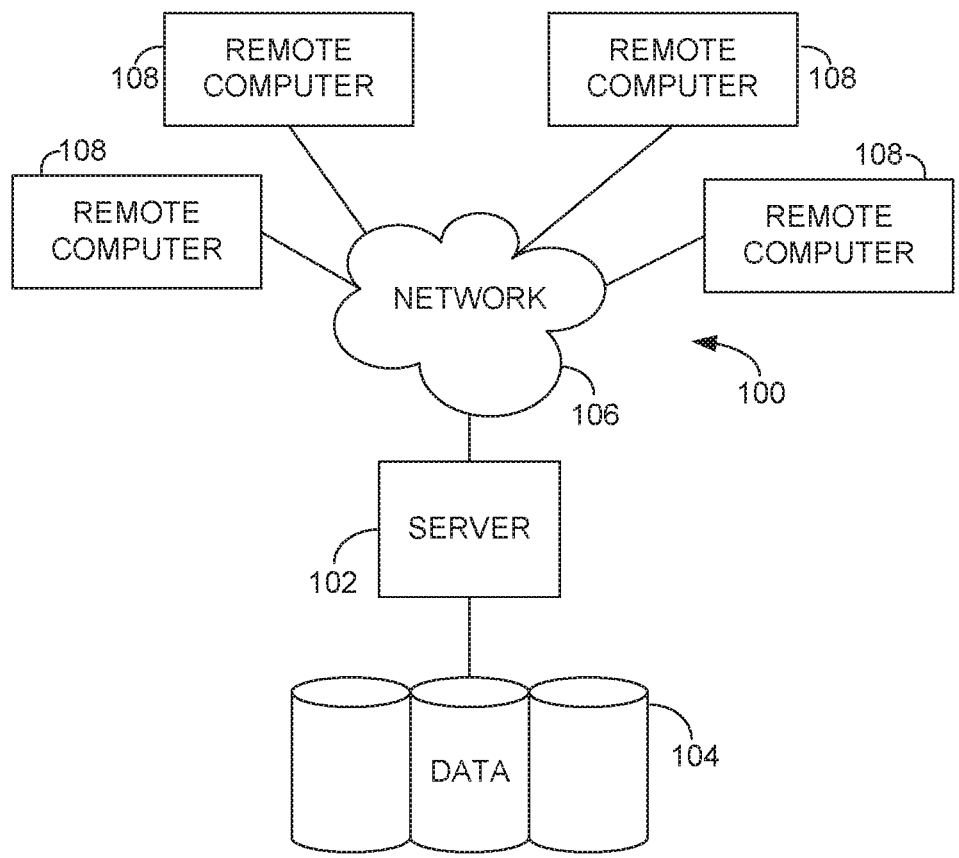
FIG. 1 is a block diagram of an exemplary computing environment suitable to implement embodiments of the present invention.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention is a special computing system that can leverage well-known computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a microphone (e.g., voice inputs), a touch screen, a pointing device (commonly referred to as a mouse), a trackball, or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Embodiments of the present invention may be implemented in a cloud-computing environment. The cloud-computing network may comprise single or multiple servers running single or multiple virtual machines. A client server with active relational database files is typically located in a location such as a pharmacy, hospital system electronic medical record, or financial services remote from an archival server or servers in a cloud-computing environment. Millions of records are transferred from the client server to the archival server or cloud-computing environment in a timely, efficient and secure manner using embodiments of the present invention.

Figure 2:
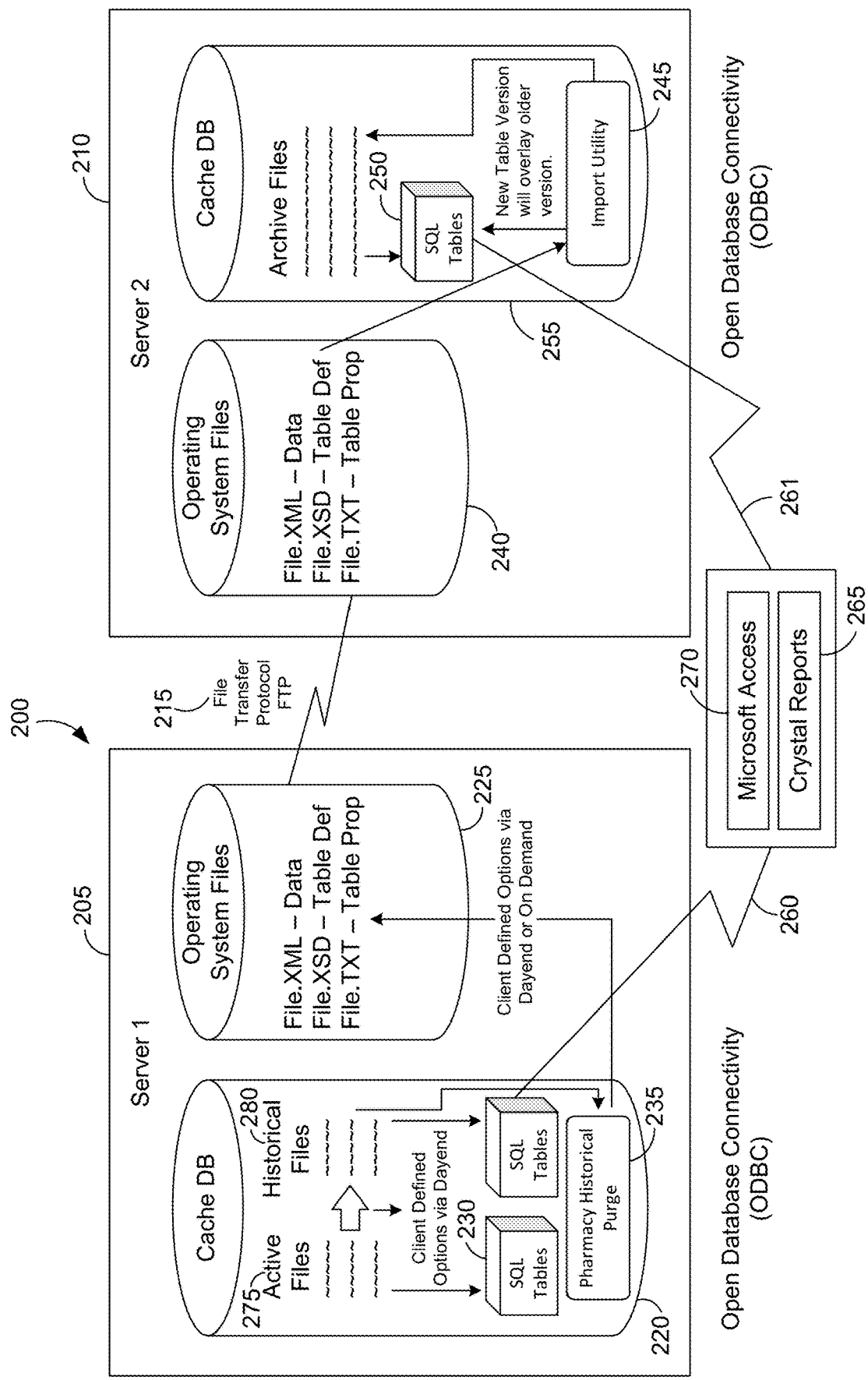
FIG. 2 is an exemplary system architecture suitable to implement embodiments of the present invention.

In an embodiment 200 exhibited by FIG. 2, a computer environment is depicted for purging and transferring historical relational database files. Client server 205 may be a variety of servers including OpenVMS and Linux servers. Client server 205 maintains active relational database files and is typically located in a location such as a pharmacy, hospital system electronic medical record, or financial services location. Client server 205 is remote from an archival server 210 such as a Microsoft Windows server in a cloud-computing environment. Client server 205 hosts a relational database system such as a Cache database 220 storing electronic medical record or electronic pharmaceutical records at a client location such as a pharmacy, hospital system electronic medical record, or financial services location. The Cache database 220 may include active relational database files 275, historical relational database files 280 and SQL tables 230. Network 215, such as the internet or other public or private network, serves as a communications link from client server 205 to archival server 210. Tasks performed by the processor utilize a variety of computer technology. In one embodiment, client server 205 is three tiers: a web server, application server and database server. Each tier is comprised of a number of system layers as described below.

Pharmacy historical purge (PHPRMAIN) 235 executes routines to access the relational database files, such as electronic medical, pharmacy and financial files. The client can define in Cache database 220 active relational database files and historical relational database files. Pharmacy historical purge 235 purges files designated as historical files from the Cache database 220. The active/historical designation allows the cache database 220 to identify active files continuously cached for performance purposes and historical files that saved are for reporting and non-immediate access. Additionally, clients do not want to purge files actively used clients for treatment of persons so the historical designation prevents purging of active files.

The Cache database 220 can create structured query language (SQL) tables 230 from both active 220 and historical 280 files for use with open database connectivity (ODBC) 260. Reporting may include Crystal Reports 265 and Microsoft Access 270 can utilize the SQL tables for reporting.

Electronic files accessed include pharmacy historical orders, pharmacy historical charges, historical medication administration charting, historical clinical interventions, historical pharmacy order enhancement, pharmacy clinical audit, pharmacy charges, medication administration charges and errors, long term care charges and claims, pharmacy historical indexes, work load statistics, user data access, centralized Masterfile tools and auditing files in Cache DB or other relational database. Pharmacy Historical Purge 220 executes routines to create operating system files 225 from the relational database files. Exemplary operating system files 225 created from the relational database files include file.xml for data, file.xsd for table definitions and file.txt for file properties. The operating system files 225 are transferred 215 using file transfer protocol 215 to archival server 210. Creating operating system files 225 and transferring files 215 using file transfer protocol can take minutes and saves hours, if not days, from prior technology that transferred relational database files line by line and the transfer prone to network interruption.

The operating system files 240 are transferred to archival server 210 and are imported into by import utility routine 245. Import utility routine 245 on archival server 210 imports the operating system files 240 and creates a relational database containing archival files in a Cache database. The structure created on the archival server is similar to that on client server 205 such that SQL tables 250 can be created from archived files so that the data can be utilized by ODBC 260 to be queried and run reports by Microsoft Access 270 and Crystal Reports 265.

Figure 3:
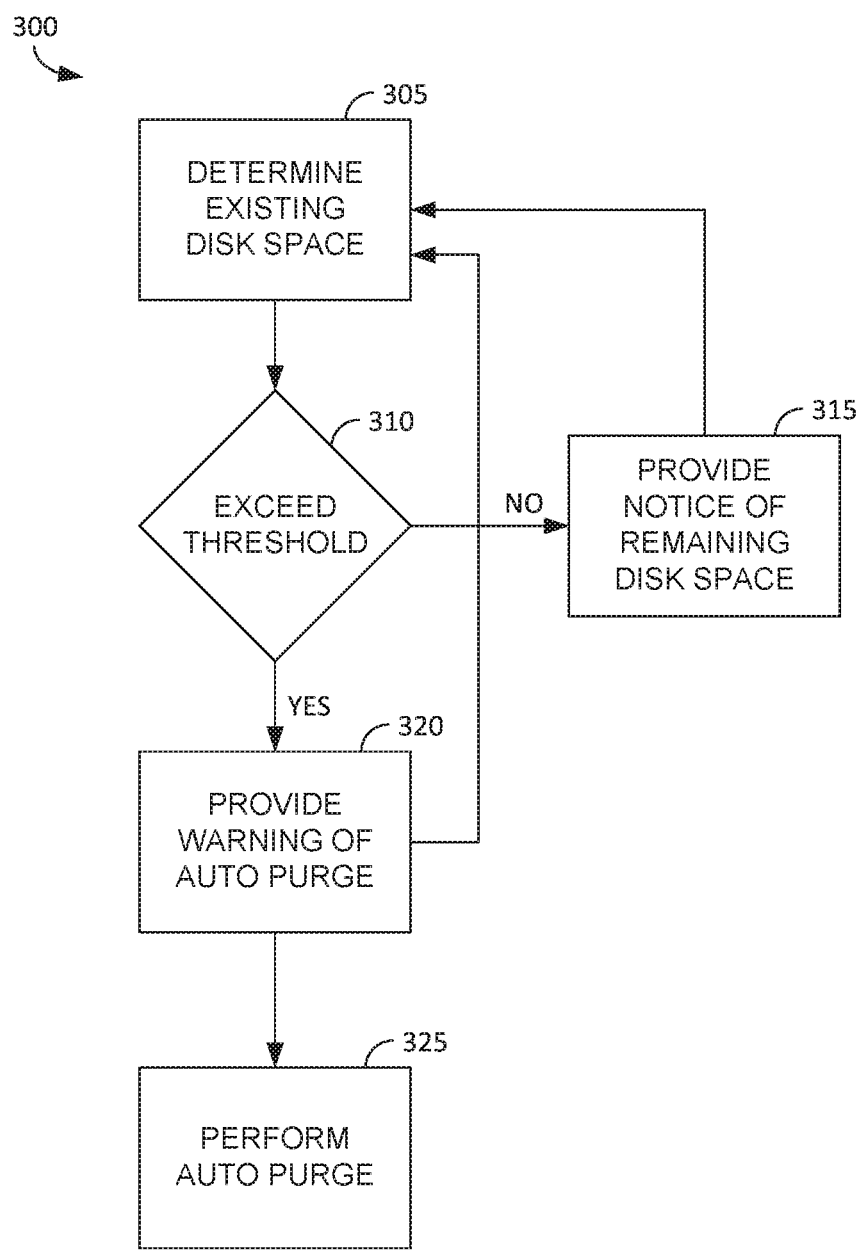
FIG. 3 is a flow diagram depicting a process for determine when disc space is full and a database is to be purged.
Figure 6:
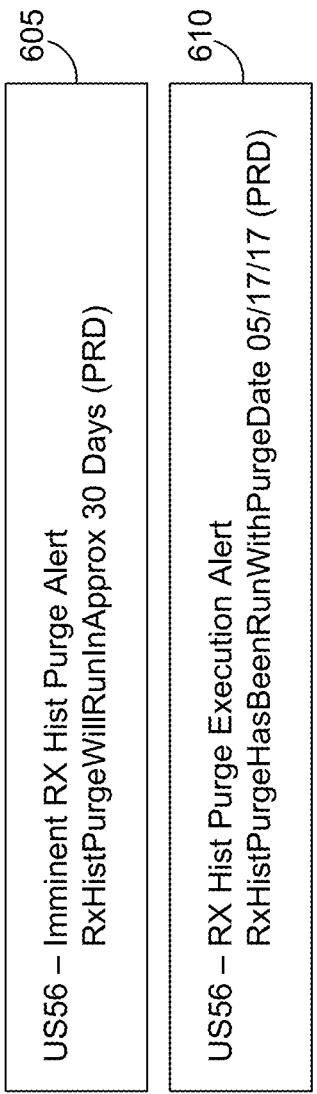
FIG. 6 depicts a graphical indicia alerting that a purge of the relational database is needed or has occurred.

FIG. 3 depicts a method for determining when to purge files from a relational database hosted on a client server, such as a medical, pharmaceutical or financial relational database. At step 305, the routine determines the amount of existing disk space available at a client server that is remote to one or more archival servers in a cloud-computing environment. At step 310, the routine determines whether the usage of the relational database exceeds the maximum allowed amount of usage for the database. The purge is performed based client defined amount of free disk space in the Cache Database. If at step 310, it is determined that the amount used exceeds the maximum threshold, a warning is provided that an auto purge of the relational database is going to occur as shown in graphical representation 605 of FIG. 6. The warning allows the client the opportunity to delay the purge or allow it to execute as defined. At step 325, an auto purge is performed on the relational database of the client server. After the purge is performed, notification 610 is provided to the client that a purge has been performed as shown in FIG. 6.

Figure 4:
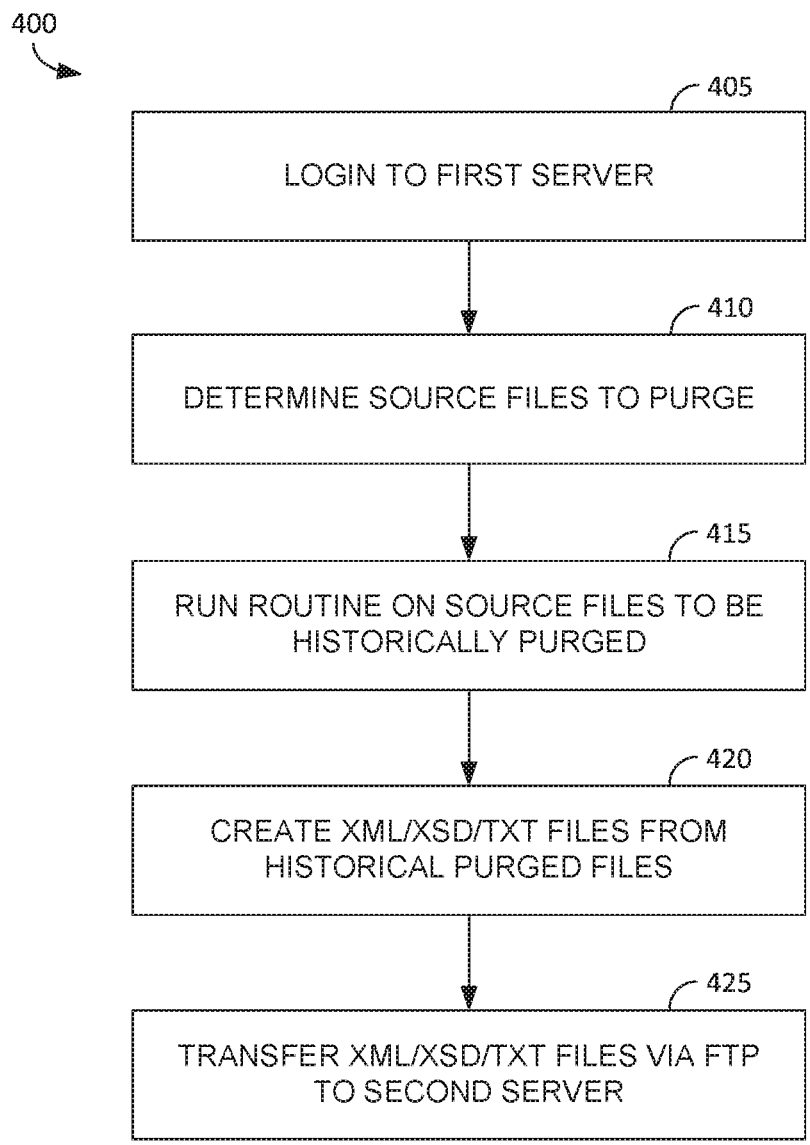
FIG. 4 is flow diagram depicting a process for creating and transferring operational database files from a relational database.

FIG. 4 depicts a method 400 for purging, converting and transferring relational database files from client server to be archived at a remote archival server. At step 410, the historical relational database files to be purged from the client are determined. These are identified by the client 405 to be purged to create more disk space on the client server. These files are typically relational database files that are not being used for current treatment or orders for a person in a pharmaceutical or medical relational database. At step 415, a routine runs on the historical relational database files to create operational database files at step 420. Relational database files are converted to operational database files such as xml, xmd and txt as described above.

Once the files to be purged are converted to operational database files they are transferred at step 425 via network using FTP to an archival server in a cloud computing network. Typically, once the transfer process is completed, the files will be purged or erased from the client server freeing up disk space for active relational database files. However, the present method and system provides a conversion to operational database files may be done as a test without deleting the files from the client server.

Figure 5:
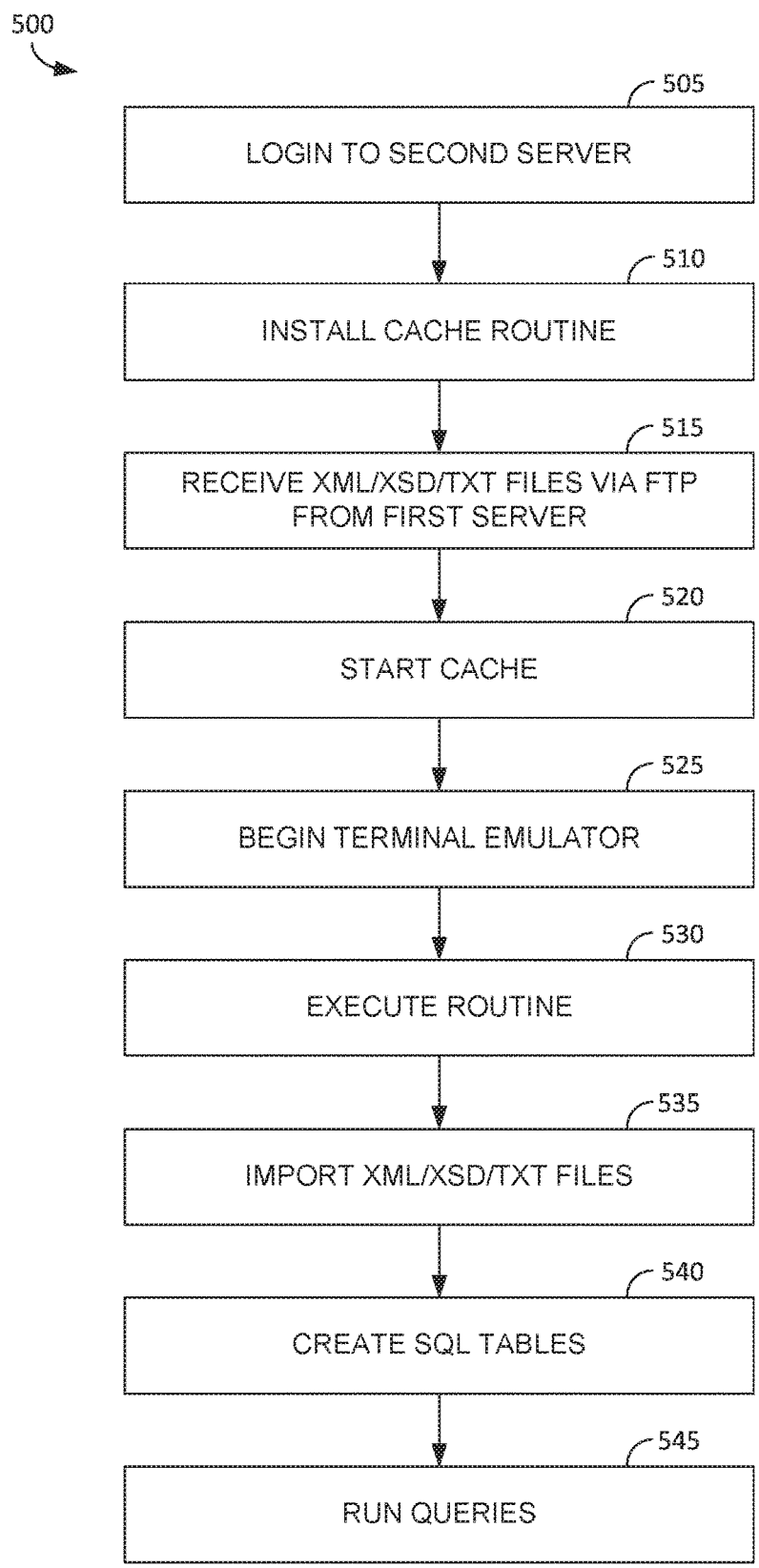
FIG. 5 is a flow diagram depicts a process for importing operational database files on a remote and creating a relational database using the files.

FIG. 5 depicts a method 500 for importing the purged operating system files (converted from relational database files) as described in FIG. 4. At step 505, a user logs into an archival server such as a server in a cloud-computing environment. For example, a user may logon to a Microsoft Windows machine on a server in a cloud-computing environment. While a Microsoft Windows machine is described, it will be appreciated that any comparable virtual operating system machine may be used.

At step 510, a cache routine is installed on the archival server. In one embodiment, UDAXML cache routine is copied and installed to the USER NameSpace on a Windows machine. The UDAXML cache routine runs the run the processing for importing the xml utility including importing the converted operating system files and converting the operating system files the specified relational database format.

At step 515, the converted operating system files are received via FTP from the first server. For example, the FTP XML/XSD/TXT files from Pharmacy server are received at c:\Temp\udaxml. A udaxml directory is created if not already defined at this step.

At step 520, Cache Studio is started and the archival server is connected to Windows for Cache Instance. It will be appreciated that while Cache Studio and cache routines are used for purposes of describing an embodiment, that any program performing the same functions could be used on the archival server. In this embodiment, Cache Studio is used on the client server hosting active relational database files and so Cache Studio is started on the archival server.

At step 525, a terminal emulator is started and import XML routine (IMPXML) is executed at step 530. The execution of IMPXML will begin the import of the operational database files (xml/xsd/txt) at step 535 previously received via FTP. It will be appreciated that XML data is loaded for the main table and global index created via input triggers table. Relational database files are created from the imported operational system files.

At step 540, SQL files are created from the imported files such that the data can be utilized by open database connectivity (ODBC). An ODBC data source name (DSN) is created for the USER NameSpace on the Windows machine. MS Access is opened such that queries and reports can be run on the structure query language files utilizing open database connectivity. Other queries and reports can be run using the open database connectivity structure of the data imported by the archival server.

Below is an example of exporting and importing the transferred relational database files. As can be seen from this example, the new process for archiving relational database files significantly reduces the amount of time needed to transfer archived files into a cloud environment, seconds or minutes using the new process vs. hours and days utilizing prior methods.

(1) Import of industry standard XML/XSD files, with Optional .TXT file
(2) Exemplary files: Clinicals, Financials, and any third party vendor
(3) Data Types are translated from Source Table to Cache Data Types
(4) Cache Package Name is configurable: AppDBType, Default=PHMMAKArchive
(5) Cache Global Prefix is configurable: Default=ARC, Example: ^ARCPHHSTORD
(6) Table Version Check is configurable: Default=1 (Do Version Check)
(7) Override Duplicate Row Data is configurable: Default=1 (Overwrite Duplicate Row Data)
(8) Only one routine to install on Windows Cache. No dependency on Sub-systems or RX App Code.
(9) USER>D IMPXML^UDAXML("C:\Temp\udaxml",,,,,1)
(10) Importing . . . C:\Temp\udaxml\PHHSTDEM_NRPRD_20160712_20160930.XSD
(11) Compilation started on May 17, 2017 15:11:37 with qualifiers 'dk', compiling 2 classes, using 8 worker jobs
(12) Compiling class PHMMAKTemp.PATNUM
(13) Compiling class PHMMAKTemp.PHHSTDEM
(14) Compiling table PHMMAKTemp.PHHSTDEM
(15) Compiling routine PHMMAKTemp.PHHSTDEM.
(16) Compilation finished successfully in 2.552 s.
(17) Exporting . . . PHMMAKTemp.PHHSTDEM to C:\Windows\Temp\PHHSTDEM.XML
(18) Exporting to XML started on May 17, 2017 15:11:40
(19) Exporting class: PHMMAKTemp.PHHSTDEM
(20) Export finished successfully.
(21) Retrieving Property Info from . . . C:\Windows\Temp\PHHSTDEM.XML
(22) LoadingC:\Windows\Temp\PHHSTDEM.XMLinto^CacheTempUserUDATMP(92
(23) Creating Dictionary Definition . . . ARCPHHSTDEM
(24) Creating UDA Table . . . PHMMAKArchive.PHHST_DEM
(25) Loading file C:\Windows\Temp\ PHHST_DEM.XML as xml
(26) Imported class: PHMMAKArchive.PHHSTDEM
(27) Compiling class PHMMAKArchive.PHHSTDEM
(28) Compiling table PHMMAKArchive.PHHST_DEM
(29) Compiling routine PHMMAKArchive.PHHSTDEM.1
(30) Load finished successfully.
(31) XML file 'C:†Windows\Temp\PHHST_DEM.XML' created successfully and imported.
(32) Deleting class PHMMAKTemp.PHHSTDEM
(33) Importing . . . C:\Temp\udaxml\ PHHSTORDERSDOCIDX_NRPRD.XSD
(34) Compilation started on May 17, 2017 15:11:41 with qualifiers 'dk', compiling 2 classes, using 8 worker jobs
(35) Compiling class PHMMAKTemp.PATNUM
(36) Compiling class PHMMAKTemp.PHHSTORDERSDOCIDX
(37) Compiling table PHMMAKTemp.PHHSTORDERSDOCIDX
(38) Compiling routine PHMMAKTemp.PHHSTORDERSDOCIDX.1
(39) Compilation finished successfully in 0.455 s.
(40) Exporting . . . PHMMAKTemp.PHHSTORDERSDOCIDX to C:\Windows\Temp\PHHSTORDERSDOCIDX.XML
(41) Exporting to XML started on May 17, 2017 15:11:42
(42) Exporting class: PHMMAKTemp.PHHSTORDERSDOCIDX
(43) Export finished successfully.

The present invention has been described in relation to particular embodiments, which are intended in all respects to be illustrative rather than restrictive. Further, the present invention is not limited to these embodiments, but variations and modifications may be made without departing from the scope of the present invention.

The invention claimed is:

1. One or more computer storage media having computer-usable instructions that, when used by one or more computing devices, cause the one or more computing devices to perform a method for exporting and purging files from a relational database, the method comprising:
   identifying the relational database files to be purged from a first server;
   converting said relational database files into operating system files;
   exporting said converted files in a batch via a network using file transfer protocol (ftp) to a remote server in a cloud computing network; and
   purging said relational database files from the first server.

2. The media of claim 1, wherein the relational database is a cache database.

3. The media of claim 1, wherein the relational database files are electronic pharmacy records.

4. The media of claim 1, wherein the relational database files are electronic medical records.

5. The media of claim 1, wherein operating system files comprise on or more of extensible markup files (xml), extended metadata (xcd) files and unformatted text (txt) files.

6. The media of claim 1, wherein operating system files comprises extensible markup files (xml), extended metadata (xcd) files and unformatted text (txt) files.

7. One or more computer storage media having computer-usable instructions that, when used by one or more computing devices, cause the one or more computing devices to perform a method for creating a relational database in a cloud computing network from importing operating system files, the method comprising:
   installing a routine on a remote hosted server to import operating system files from a first server via a network and create a relational database with said operating system files;
   beginning a terminal emulator for the relational database;
   executing said routine to import said operating system files; and
   executing said routine to create the relational database on the remote hosted server using said operating system files.

8. The media of claim 7, wherein the relational database is a cache database.

9. The media of claim 7, wherein the relational database files are electronic pharmacy records.

10. The media of claim 7, wherein the relational database files are electronic medical records.

11. The media of claim 7, wherein operating system files comprise on or more of extensible markup files (xml), extended metadata (xcd) files and unformatted text (txt) files.

12. The media of claim 7, wherein operating system files comprises extensible markup files (xml), extended metadata (xcd) files and unformatted text (txt) files.

13. One or more computer storage media having computer-usable instructions that, when used by one or more computing devices, cause the one or more computing devices to perform a method for purging files from a relational database and creating a relational database from said purged files on a remote server, the method comprising:
   identifying the relational database files to be purged from a first server;
   converting said relational database files into operating system files;
   exporting said converted files in a batch via a network using file transfer protocol (ftp) to a remote server in a cloud computing network;
   purging said relational database files from the first server;
   installing a routine on the remote hosted server to import operating system files from a first server via a network and create a relational database with said operating system files;
   beginning a terminal emulator for the relational database;
   executing said routine to import said operating system files; and
   executing said routine to create the relational database on the remote hosted server using said operating system files.

14. The media of claim 13, wherein the relational database is a cache database.

15. The media of claim 13, wherein the relational database files are electronic pharmacy records.

16. The media of claim 13, wherein the relational database files are electronic medical records.

17. The media of claim 13, wherein operating system files comprise on or more of extensible markup files (xml), extended metadata (xcd) files and unformatted text (txt) files.

18. The media of claim 13, wherein operating system files comprises extensible markup files (xml), extended metadata (xcd) files and unformatted text (txt) files.

19. The media of claim 18, further comprising:
   creating Structured Query Language files from the relational database on the remote hosted server using said operating system files; and
   creating structured query language files from files not purged from the first server.

20. The media of claim 19, further comprising:
   running reports on the structure query language files from both the remote hosted server and the first server.

* * * * *